US008414912B2

(12) United States Patent
Ciolino et al.

(10) Patent No.: US 8,414,912 B2
(45) Date of Patent: Apr. 9, 2013

(54) CONTACT LENS DRUG DELIVERY DEVICE

(75) Inventors: Joseph B. Ciolino, Boston, MA (US);
Todd R. Hoare, Cambridge, MA (US);
Daniel S. Kohane, Newton, MA (US)

(73) Assignees: Massachusetts Institute of Technology, Cambridge, MA (US); Children's Medical Center Corporation, Boston, MA (US); Massachusetts Eye and Ear Infirmary, Boston, MA (US)

( * ) Notice: Subject to any disclaimer, the term of this patent is extended or adjusted under 35 U.S.C. 154(b) by 379 days.

(21) Appl. No.: 12/636,671

(22) Filed: Dec. 11, 2009

(65) Prior Publication Data
US 2010/0239637 A1    Sep. 23, 2010

Related U.S. Application Data

(60) Provisional application No. 61/121,806, filed on Dec. 11, 2008.

(51) Int. Cl.
*A61K 9/00*     (2006.01)

(52) U.S. Cl.
USPC ......................................................... 424/429

(58) Field of Classification Search .................. None
See application file for complete search history.

(56) References Cited

U.S. PATENT DOCUMENTS

| | | | |
|---|---|---|---|
| 3,618,604 A | 11/1971 | Ness | |
| 3,710,796 A | 1/1973 | Neefe | |
| 3,786,812 A | 1/1974 | Neefe | |
| 3,828,777 A | 8/1974 | Ness | |
| 3,854,480 A | 12/1974 | Zaffaroni | |
| 3,957,049 A | 5/1976 | Neefe | |
| 4,484,922 A | 11/1984 | Rosenwald | |
| 5,318,780 A | 6/1994 | Viegas et al. | |
| 6,027,745 A | 2/2000 | Nakada et al. | |
| 6,101,411 A | 8/2000 | Newsome | |
| 6,284,161 B1 | 9/2001 | Thakrar et al. | |
| 2003/0203032 A1 | 10/2003 | Schultz | |
| 2004/0241207 A1* | 12/2004 | Chauhan et al. | 424/429 |
| 2005/0025810 A1 | 2/2005 | Peyman | |
| 2005/0147685 A1 | 7/2005 | Osada et al. | |
| 2005/0196428 A1 | 9/2005 | Schultz | |
| 2006/0187410 A1 | 8/2006 | Sato et al. | |
| 2006/0251696 A1 | 11/2006 | Winterton et al. | |
| 2008/0075757 A1 | 3/2008 | Chauhan et al. | |
| 2008/0107713 A1 | 5/2008 | Orilla et al. | |
| 2008/0138408 A1* | 6/2008 | Venkatesh et al. | 424/464 |
| 2009/0004245 A1* | 1/2009 | Orilla et al. | 424/429 |

FOREIGN PATENT DOCUMENTS

| | | | |
|---|---|---|---|
| DE | 2308144 | * | 8/1974 |
| DE | 2308144 A1 | | 8/1974 |
| WO | WO 2006/014138 A1 | | 2/2006 |
| WO | WO 2010/068281 A2 | | 6/2010 |

OTHER PUBLICATIONS

Kim et al. "Extended delivery of ophthalmic drugs by silicone hydrogel contact lenses", Biomaterials, 29, 2008, pp. 2259-2269.*
Ali et al. "Zero-order therapeutic release from imprinted hydrogel contact lenses within in virtro physiological ocular tear flow" Journal of Controlled Release, 124, 2007, pp. 154-162.*
Innovadex "Panodan SDK" http://www.innovadex.com/Food/Detail/3913/111473/PANODAN-SD-D-K-801335?st=20&sl=0&crit=SW50ZXJuZXQgU2VhcmNhID4gRGFuaXNjbyBVU0EgSW5jLi AtIEVtdWxzaWZpZXJz, accessed Nov. 28, 2011.*
Ali, M. et al., "Zero-order Therapeutic release from imprinted hydrogel contact lenses within in vitro physiological ocular tear flow," *Journal of Controlled Release*, 2007, 124, 154-162.
Ciolino, J. et al., "A Drug-Eluting Contact Lens," *Investigative Ophthalmology & Visual Science*, 2009, 50(7), 3346-3352.
Ciolino, J. et al., "Contact Lens Drug Delivery," Poster presented at Association for Research in Vision and Ophthalmology 2009 Annual Meeting, May 7, 2009.
Ciolino, J. et al., "Contact Lenses for Drug Delivery," *Seminars in Ophthalmology*, 2009, 24(3), 156-160.
Hoare, T. et al., "Hydrogels in drug delivery: Progress and challenges," *Polymer*, 2008, 49, 1993-2007.
Sano, K. et al., "A new drug delivery system utilizing piggyback contact lenses," *The Ophthalmological Journal of the Nordic Countries*, 1996, 74(3), 243-248.
Winterton, L. et al., "The Elution of Poly (vinyl alcohol) From a Contact Lens: The Realization of a Time Release Moisturizing Agent/Artificial Tear," *Journal of Biomedical Materials Research Part B: Applied Biomaterials*, 2007, 424-432.
Kim, J. et al., "Extended delivery of ophthalmic drugs by silicone hydrogel contact lenses," *Biomaterials*, 2008, 29, 2259-2269.
Hiratani, H. et al., "Controlling Drug Release from Imprinted Hydrogels by Modifying the Characteristics of the Imprinted Cavities," *Macromolecular Bioscience*, 2005, 5, 728-733.
Venkatesh, S. et al., "Biomimetic Hydrogels for Enhanced Loading and Extended Release of Ocular Therapeutics," *Biomaterials*, 2007, 28(4), 717-724.
International Search Report and Written Opinion mailed Jan. 24, 2011 for Related International Application No. PCT/US2009/006507.
Karlgard, C.C.S., et al., "In vitro uptake and release studies of ocular pharmaceutical agents by silicon-containing and p-HEMA hydrogel contact lens materials," *International Journal of Pharmaceutics* 257 (2003) pp. 141-151.

* cited by examiner

*Primary Examiner* — Daniel Sullivan
*Assistant Examiner* — Melissa Javier
(74) *Attorney, Agent, or Firm* — Wolf, Greenfield & Sacks, P.C.

(57) ABSTRACT

The present invention relates generally to devices and methods for administering one or more active agents to the eye of a human or animal patient in need thereof, and more particularly to devices for application to the cornea which release active agent to the eye in a controlled manner.

32 Claims, 6 Drawing Sheets

CONTACT LENS DRUG DELIVERY DEVICE

RELATED APPLICATIONS

This application claims the benefit of U.S. Provisional Patent Application Ser. No. 61/121,806, filed Dec. 11, 2008, entitled "Contact Lens Drug Delivery Device," by Ciolino et al., incorporated herein by reference.

FIELD OF THE INVENTION

The present invention relates generally to devices and methods for administering one or more active agents to the eye of a human or animal patient in need thereof, and more particularly to devices for application to the cornea which release active agent to the eye in a controlled manner.

BACKGROUND OF THE INVENTION

Topical ophthalmic solutions, or eye drops, are currently the most commonly used method of ocular drug delivery. Eye drops account for approximately 90% of all ophthalmic medications, but are very inefficient. Eye drops are administered by pulse delivery, which is characterized by a transient overdose, followed by a relatively short period of effective therapeutic concentration, and then a prolonged period of insufficient concentration or under-dosing. Furthermore, each drop is diluted and washed away by reflex tearing and blinking so that only 1 to 7% of an eye drop is absorbed by the eye. The remainder is either flushed onto the patient's cheek or drained through the nasolacrimal system.

Ophthalmic ointments, which are viscous semisolid preparations, may be the most commonly used alternative to liquid eye drops. Due to their greater viscosity, ointments have a longer contact time with the cornea and possibly provide more opportunity for drug absorption than a solution. The viscous nature of ointments, however, distorts and blurs the patient's vision. Injections into the vitreous, subconjunctival space, and sub Tenon's space are also alternative methods of drug delivery for some medications. Due to the associated discomfort, risk of infection, and lack of patient enthusiasm for ocular injections, however, drug delivery by injection is typically reserved for drugs which have poor water solubility or cannot be adequately delivered by topical means. There remains a need to increase the availability of medications to the eye, to increase the exposure time of the medication to the eye, and to more effectively deliver to the eye drugs that cannot be applied effectively and efficiently as topical drops.

The concept of delivering a medication to the eye through a contact lens was introduced as early as 1960. While the uptake and release of medications from conventional soft contact lenses has been explored, there remains a need to provide a contact lens device that can deliver drug to the eye in a controlled, sustained release manner. Furthermore, it would be desirable to provide a contact lens drug delivery device that is relatively simple in design, that does not require complicated and expensive manufacturing processes, that does not significantly impair or interfere with the patient's vision, and that would not require a substantial change in the practice patterns of eye physicians and surgeons. It would also be desirable for the drug delivery device in use to be substantially unnoticeable to the casual observer of the patient.

SUMMARY OF THE INVENTION

Improved devices and methods for controlled drug delivery are provided. The subject matter of the present invention involves, in some cases, interrelated products, alternative solutions to a particular problem, and/or a plurality of different uses of one or more articles and/or methods.

In one aspect, a drug-eluting contact lens is provided. The contact lens comprises a drug release material comprising at least one drug, wherein the contact lens provides substantially zero-order release of the at least one drug over a period of at least 120 hours, wherein the at least one drug is released at a rate of at least 0.01 micrograms per hour.

In another aspect, a drug-eluting contact lens is provided. The contact lens comprises an optical pathway wherein the line of vision of a wearer of the contact lens passes through the pathway. The contact lens further comprises a substantially continuous drug carrying zone comprising at least one drug for release by the contact lens proximate the eye, the zone surrounding the optical pathway but not residing in the optical pathway, wherein the drug carrying zone is encapsulated by a lens material.

In yet another aspect, a drug-eluting contact lens is provided. The drug eluting contact lens comprises a drug release material comprising at least one drug, and constructed and arranged to release the drug from the material proximate the eye, wherein the drug is present in the contact lens in an amount of at least about 2 mg.

In still another aspect, a drug-eluting contact lens is provided. The drug eluting contact lens comprises a drug release material comprising at least one drug, and constructed and arranged to release the drug from the contact lens proximate the eye at a rate of at least 1 microgram per hour, for a period of time of at least 120 hours.

In yet another aspect, a drug-eluting contact lens is provided. The drug eluting contact lens comprises a drug release material comprising at least one drug, and constructed and arranged to release the drug from the contact lens proximate the eye for a period of at least 120 hours at controlled rate such that at the 120th hour the lens releases the at least one drug at a rate of at least 0.05 micrograms per hour.

In still another aspect, a drug-eluting contact lens is provided. The drug eluting contact lens comprises a drug release material comprising at least one drug. The drug eluting contact lens further comprises a hydrogel lens material encapsulating the drug release material, wherein the contact lens provides controlled release of the at least one drug to a patient's eye.

In yet another aspect, a drug-eluting contact lens is provided. The drug eluting contact lens comprises a single drug release material surrounding the optical axis of the contact lens, the drug release material including a polymer in which at least one drug is dispersed. The contact lens further comprises a hydrogel lens material encapsulating the drug release material, wherein the contact lens, when placed onto a patient's eye, provides controlled release of the at least one drug to the patient's eye.

In still another aspect, a drug-eluting contact lens is provided. The drug eluting contact lens comprises a hydrogel lens material encapsulating a drug-containing polymer film, wherein the contact lens provides substantially zero-order release of the at least one drug for at least 168 hours.

In yet another aspect, a drug-eluting contact lens is provided. The drug eluting contact lens comprises a hydrogel lens material encapsulating a drug-containing polymer film, wherein the contact lens provides release of the at least one drug at therapeutically effective amounts for at least 168 hours.

In still another aspect, a packaged medical device is provided. The packaged medical device comprises at least one of the drug-eluting contact lenses mentioned above and a packaging container which contains (i) said at least one drug-eluting contact lens, and (ii) a saturated solution of drug which is the same drug as the at least one drug in the drug-containing polymer film of said at least one drug-eluting contact lens.

In yet another aspect, a packaged medical device is provided. The packaged medical device comprises at least one of the drug-eluting contact lenses mentioned above, which is in a lyophilized or otherwise partially or completely dehydrated state. The packaged medical device further comprises a packaging container which contains said at least one drug-eluting contact lens, said packaging container being sealed and capable of maintaining the at least one drug-eluting contact lens in its lyophilized state.

In still another aspect, a method for administering a drug to the eye of a patient is provided. The method comprises applying any of the drug-eluting contact lenses mentioned above onto the cornea of the patient's eye. The method further comprises permitting the at least one drug to be released from the contact lens to the patient's eye in a therapeutically or prophylactically effective amount.

In yet another aspect, a method for administering a drug to the eye of a patient is provided. The method comprises implanting into the cornea of the patient's eye a device which comprises (i) a drug release material comprising at least one drug, and (ii) a hydrogel lens material encapsulating the drug release material. The method further comprises permitting the at least one drug to be controllably released from the implanted device to the patient's eye in a therapeutically or prophylactically effective amount.

In still another aspect, a method for administering a drug to the eye of a patient is provided. The method comprises surgically suturing to the sclera of the patient's eye a device which comprises (i) a drug release material comprising at least one drug, and (ii) a hydrogel lens material encapsulating the drug release material. The method further comprises permitting the at least one drug to be controllably released from the implanted device to the patient's eye in a therapeutically or prophylactically effective amount.

In yet another aspect, a method for prophylaxis or treatment of eye infections in a patient is provided. The method comprises applying any of the drug-eluting contact lenses mentioned above onto the cornea of the patient's eye, wherein the at least one drug comprises an anti-infective agent. The method further comprises releasing the at least one anti-infective agent from the contact lens to the patient's eye in a therapeutically or prophylactically effective amount for at least 24 hours.

In still another aspect, a method of making a contact lens drug delivery device is provided. The method comprises forming a polymer-drug film. The method further comprises encapsulating the polymer-drug film within a hydrogel lens material in the shape of a lens.

In yet another aspect, a structure for controlled drug delivery as described herein is provided.

In still another aspect, a drug-eluting contact lens is provided. The contact lens comprises a drug-containing film which includes at least one drug combined with a non-polymeric excipient material. The contact lens further comprises a lens material encapsulating the drug-containing film, wherein the contact lens provides controlled release of the at least one drug to a patient's eye.

In yet another aspect, a scleral lens is provided. The scleral lens comprises a rigid lens portion, and a drug releasing depot portion which comprises a drug release material comprising at least one drug. The scleral lens further comprises a hydrogel lens material encapsulating the drug release material, wherein the drug releasing depot portion is secured to the rigid lens such that the depot portion is disposed between the rigid lens and the patient's cornea when the scleral lens is worn.

In still another aspect, a device constructed and arranged for use in the eye is provided. The device comprises a drug release material comprising at least one drug, and constructed and arranged to release the drug from the device proximate the eye for a period of at least 120 hours at controlled rate such that at the 120th hour the device releases the at least one drug at a rate of at least 0.05 micrograms per hour.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. It should be understood that a day is equivalent to 24 hours. It should also be understood that where multiple days are provided, the days can be converted to hours by multiplying the number of days by 24 hours. In the figures.

Figure 1:
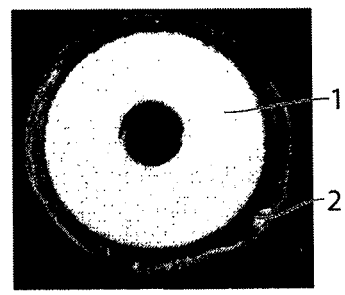
FIG. 1 is a photograph of a prototype drug delivery device made of pHEMA hydrogel, the pHEMA encapsulating a PLGA film containing ciprofloxacin with a 5 mm clear optical aperture.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Improved drug delivery devices have been developed for administering a drug or other active agent to the ocular region. In one aspect, the device is a drug eluting contact lens which can be applied to a patient's cornea. In one embodiment, the contact lens device comprises a drug release material comprising at least one drug and a hydrogel lens material encapsulating the drug release material. It has been discovered that this structure advantageously can provide controlled release of the drug, with substantially zero order release kinetics, over an extended period of time. In some embodiments, the structure beneficially enables the contact lens to be loaded with a high level of drug, yet premature or uncontrolled leakage of the drug may be essentially avoided. In one embodiment, the lens material surrounding the drug release material has a substantially uniform composition. In a particular embodiment, the device has a single drug release material, which surrounds the optical axis of the contact lens. The contact lens device advantageously can provide sustained release of therapeutically or prophylactically effective amounts of the drug over an extended period. In one embodiment, the controlled release of the drug from the contact lens is substantially zero-order over the period during which a therapeutically or prophylactically effective amount of the drug is released.

In some embodiments, the drug delivery device includes a drug release material comprising at least one active agent (e.g, a drug) and a hydrogel lens material encapsulating the drug release material comprising the at least one active agent. The device generally may be provided in any configuration or geometry that would be suitable for a given ocular or non-ocular use.

In one aspect, the device is in the shape of a contact lens. That is, the device may be a drug-eluting contact lens. In one embodiment, the contact lens is structured and dimensioned so that, when worn by the patient, the contact lens will touch the conjunctiva with the drug release material disposed at least partially under the eyelid. In other embodiments, the contact lens may be designed to avoid one or both of these anatomical landmarks. The lens device may be powered or plano.

In certain embodiments, the contact lens device may be provided with structural features to impart directional control over the release of the drug. For example, the contact lens device may include micro-perforations, selected areas of varying thickness and permeability, or any combination thereof, which may for example facilitate mass transport of the drug by reducing diffusional distances or enabling bulk fluid flow through portions of the device rather than having to rely solely on diffusional mass transport.

The contact lens device may deliver more than one type of drug simultaneously. In one embodiment, the contact lens device includes a second drug, which may be incorporated into the drug release material, the hydrogel lens material, or both. It should be understood that the contact lens may contain a third drug, fourth drug, or even more drugs.

In one embodiment, the contact lens device has a single drug release material. In a particular embodiment, the area of the drug release material in the contact lens device is coextensive with more than 1%, more than 5%, more than 10%, more than 20%, more than 50%, or more than 75%, of the area of the hydrogel lens material when the contact lens device is viewed along the optical axis.

In some embodiments, the drug release material includes a release agent in which at least active agent (e.g., a drug) is mixed. The mixture may be a homogenous mixture or a heterogenous mixture. In one embodiment, the drug is insoluble and dispersed in the release agent. In another embodiment, the drug and release agent are in the form of a solid solution. For example, the solid solution may be made by using a solvent system, e.g., co-solvents, in which the release agent and drug are both solubilized. As discussed in more detail below, in some embodiments, the release agent may comprise a polymer and/or a non-polymeric excipient.

In some embodiments, the drug release material may be configured as a film. As used herein, the term "film" means a thin, preferably flexible, monolithic sheet of material having a thickness from 50 nm to 500 µm. In one embodiment, the film is from about 1 µm to 500 µm. In one embodiment, the film has a thickness from about 10 µm to about 100 µm. A layer comprising a collection of microparticles is not a film; however, the drug release material may comprise a collection of particles such as microparticles and/or nanoparticles.

Generally, the drug release materials of the device described herein may be fashioned into various shapes and sizes. In certain embodiments, the drug release material is circular or ring shaped, or semi-circular, crescent-shaped, or arch-shaped. In one embodiment, the drug release material includes an aperture about the optical axis of the contact lens. In one embodiment, the drug release material may have a multi-layer structure. In one case, the drug release material may include a coating on one or both sides, for example, with a polymer containing no drug or less or more drug than the drug release material. The drug release material may comprise a single film or a stack of two or more films.

Figure 2A:
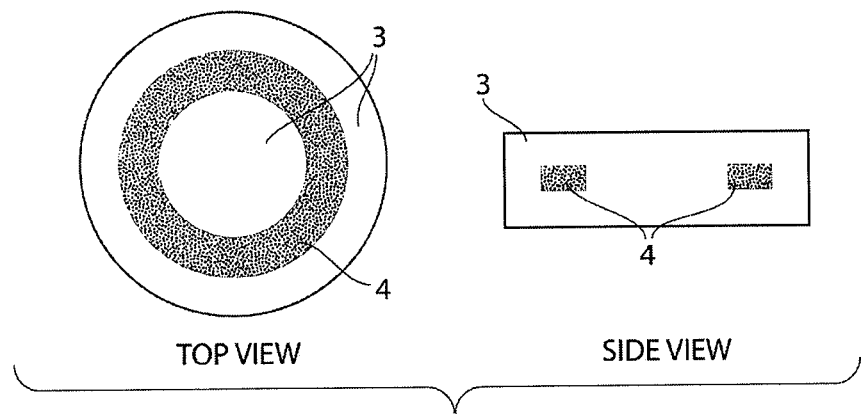
FIG. 2a is a schematic of a prototype drug delivery device with a ring-shaped drug release material.
Figure 2B:
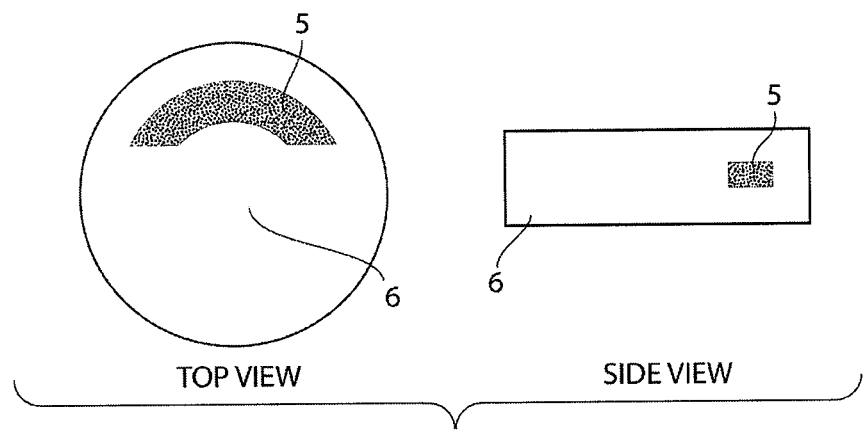
FIG. 2b is a schematic of a prototype drug delivery device with an arch- or crescent-shaped drug release material.

In a particular embodiment, the drug release material 4 encapsulated in the hydrogel 3 is in the shape of ring as shown in FIG. 2a. The drug release material of this embodiment includes a central aperture. Typically, the aperture corresponds with the optical axis of the patient's eye. The drug release material may also be formed in a number of other suitable geometries and configurations. In another embodiment, the drug release material 5 may be arch- or crescent-shaped, as shown in FIG. 2b. The encapsulating hydrogel 6 of this embodiment may be fabricated with a diameter large enough to conceal the drug release material 5 under the patient's upper and/or lower eyelid, and at least partially over the patient's conjunctiva. Various factors may be considered when determining the desired size and shape of the drug release material, including but not limited to cosmesis, oxygen permeability, and obstruction of the patient's vision.

The mass ratio of release agent to drug in the drug release material may vary widely, depending, for example, on the particular drug and treatment, the selected polymer and/or non-polymeric excipient of the drug release material, the desired kinetics of drug release, and/or the dosage needed for therapeutic efficacy. Other factors may also influence the choice of mass ratio of release agent to drug in the drug release material. In one embodiment, the ratio may be from about 1000:1 to about 1:1000. In one example, the release agent:drug ratio may be at least 1000:1 for a highly potent therapeutic compound. In some embodiments, the mass ratio of release agent to drug in the drug release material is from about 2:1 to about 1:2, from about 10:1 to about 1:10, or about 100:1 to about 1:100.

In some embodiments, the drug release material forms a substantially continuous drug carrying zone. In some cases, the substantially continuous drug carrying zone surrounds the optical pathway of a contact lens but does not reside in the optical pathway. In one embodiment, the composition of the drug release material is substantially uniform. In another embodiment, a first zone of the drug release material have a different composition than a second zone of the drug release material. For example, the drug release material may have discrete drug carrying zones (i.e., regions) of higher or lower amounts of drug loading in the drug release material. In one embodiment, there may be a gradient of the drug loading. In some embodiments, a first drug carrying zone of the drug release material may contain a first drug, and a second drug carrying zone of the drug release material may be contain a second drug, the second drug being different from the first drug.

In some cases, a drug release material may comprise a plurality of layers where each layer contains a different ratio of release agent:drug. In some embodiments, at least one of the layers may consist essentially of one or more drugs. In some cases, at least one of the layers may consist essentially of one or more polymers. A layer may contain mixture of two or more polymers, and a first layer may contain a different polymer than a second layer. In one embodiment, a layer may be colored, for example, to change the color appearance of the iris.

The device may be used to deliver essentially any active agent (e.g., a drug), including for example small molecule drugs, proteins, nucleic acids, polysaccharides, and biologics. The drug may be any agent capable of providing a therapeutic benefit. In an embodiment, the drug is a known drug, or drug combination, effective for treating diseases and disorders of the eye. In non-limiting, exemplary embodiments, the drug is an antiinfective agent (e.g., an antibiotic or antifungal agent), an anesthetic agent, an anti-VEGF agent, an anti-inflammatory agent, a biological agent (such as RNA), an intraocular pressure reducing agent (i.e., a glaucoma drug), or a combination thereof. Non-limiting examples of drugs are provided below.

Release characteristics of the drug may impact the design choice of drug in particular applications. For example, as an alternative to ciprofloxacin, an antibiotic with greater potency may be used. Non-limiting examples of such potent alternatives include ofloxacin, gatifloxacin, and levofloxacin. These alternative fluoroquinalones also have greater water solubility than ciprofloxacin. Timolol maleate is another very potent drug with several alternatives, including, but not limited to, dozolamide hydrochloride and latanoprost. Compared to timolol maleate, dorzolamide hydrochloride is more water soluble while latanoprost is less water soluble. Therefore, without wishing to be bound by any theory, the water solubility of the drugs and their alternatives may play an role in deciding which drug to incorporate into the presently disclosed drug delivery devices.

The polymer in the drug release material is essentially any biocompatible polymer, co-polymer, terpolymer, or polymer blend. In one aspect, the polymer of the drug release material is biodegradable. In one embodiment, the products of the polymers' degradation should not pose a health risk to the ocular region.

Biodegradability of the polymer in the drug release material is typically not a primary consideration except to the extent that the degradation may promote the desired release of the drug. Generally, both biodegradable and non-biodegradable polymers may be used to create drug polymer films that function desirably in the devices described herein.

In one embodiment, the polymer of the drug release material is biodegradable. For example, the polymer of the drug release material may be poly(lactic-co-glycolic) acid ("PLGA"), polylactide, polyglycolide, polycaprolactone, or other polyesters, poly(orthoesters), poly(aminoesters), polyanhydrides, polyorganophosphazenes, or any combination thereof. Other biodegradable polymers known to those skilled in the art may also be applied and selected based on the desired mechanical properties and polymer-drug interaction.

In another embodiment, the polymer of the drug release material is non-degradable. For example, the polymer of the drug release material may be ethyl cellulose, poly(butyl acrylate), poly(urethanes), silicone resins, nylon, ammonium polyacrylate, acrylamide copolymers, acrylate/acrylamide copolymers, acrylate/ammonium acrylate copolymers, acrylate/alkyl acrylate copolymers, acrylate/carbamate copolymers, acrylate/dimethylaminoethyl methacrylate copolymers, ammonium acrylate copolymers, styrene/acrylate copolymers, vinyl acetate/acrylate copolymers, aminomethylpropanol/acrylate/dimethylaminoethylmethacrylate copolymers, or any combination thereof. Other non-degradable polymers known to those skilled in the art may also be applied and selected based on the desired mechanical properties and polymer-drug interaction.

In some embodiments, the drug release material may comprise a hydrogel. Examples of hydrogels include, but are not limited to, polyhydroxyethylmethacrylate (pHEMA), a silicone, agarose, alginate, chitosan, and hyaluronic acid. Other hydrogels known to those skilled in the art may also be applied and selected based on the desired mechanical properties and hydrogel-drug interaction. The drug release material may, in some cases, form a gel within a pH range. In another embodiments, the drug release material may transition between a liquid and a gel at a critical temperature.

In an alternative embodiment, the polymer of the drug release material may be replaced with a non-polymeric excipient. For example, the drug release material may be a sugar. In one embodiment, the drug release material may be sucralfate. Other examples of excipients are provided below.

Generally, the lens material used to encapsulate the drug release material may be any biocompatible material suitable for ocular or non-ocular medical uses. In one embodiment, the lens material is a hydrogel known in the art of soft contact lenses. For example, in various embodiments, the lens material may comprise polyhydroxyethylmethacrylate (pHEMA), a silicone, or a composite comprising silicone dispersed in a hydrogel. In one embodiment, the hydrogel comprises polyhydroxyethylmethacrylate (pHEMA) or co-polymers thereof. In another embodiment, the hydrogel comprises a silicone hydrogel. In still another embodiment, the hydrogel comprises hyaluronic acid. The hydrogels may be cross-linked using methods and/or materials known in the art, which are suitable for use with the ocular tissues. In one embodiment, the cross-linking agent is ethyleneglycol dimethacrylate (EGDMA).

In an alternative embodiment, the lens material comprises a non-hydrogel material. The non-hydrogel material may have suitable oxygen, water, and drug permeability properties to permit its use as a contact lens. In some embodiments, the lens material is a material known in the art of hard contact lenses (i.e., rigid gas permeable lenses). Hard contact lenses may or may not have perforations.

The lens material used to encapsulate the drug release material may be any material with sufficient oxygen permeability to allow for the patient to safely wear the contact lens device for the period of desired administration of the drug, e.g., for the duration of treatment or prophylaxis needed. Depending on the oxygen permeability (i.e., Dk value) of the hydrogel material used, the contact lens device may be worn continually. The lens material may have, in some embodiments, a Dk value greater than 5, greater than 10, greater than 15, greater than 20, greater than 30, greater than 60, greater than 90, greater than 100, or even greater. In one embodiment, the oxygen permeability is such that the contact lens device is suitable for daily ocular wear. For instance, the hydrogel material may have a Dk value of at least 5.25.

In some embodiments, the lens material has a water content of at least 20%, at least 30%, at least 40%, at least 50%, at least 60%, or at least 70%. In some cases, the water content is between 40% and 60%.

In some embodiments, device may be worn from 1 to 2400 hours. In certain embodiments, the lens material is sufficiently oxygen permeable to allow the contact lens device to be worn by the patient continuously for at least 24 hours, for at least 72 hours, for at least 120 hours, for at least 240 hours, for at least 336 hours, for at least 480 hours, or for at least 720 hours.

It should be understood that a day is equivalent to 24 hours. It should also be understood that where multiple days are provided, the days can be converted to hours by multiplying the number of days by 24 hours.

In some embodiments, the contact lens device may also be worn for at least 1 hour, at least 2 hours, at least 4 hours, at least 8 hours, at least 16 hours, or even longer. In some cases, the device may be removed at least twice per day, at least once per day, at least once per week, or at least once per month. The device may be removed with other frequencies as well. After removal of the device, the same contact lens device may be re-inserted (e.g., after cleaning and/or sanitizing), or a new contact lens device may be inserted.

In one embodiment, the lens material is optically transparent, at least at a position about the contact lens device's optical axis.

In one embodiment, the lens material also includes a drug for release. It may be mixed into the lens material precursor before encapsulating the drug release material, or it may be load into the lens material following the encapsulation process. The drug in the lens material may be the same as or a different from the drug(s) provided in the drug release material. In one embodiment, this drug located in a hydrogel lens material may be released substantially immediately upon application of the lens device to the eye, giving the drug in the drug release material time to diffuse from the film and through the lens, thereby providing for example an initial dose and follow-on sustained release, or maintenance dose.

The drug release material and the lens material may control the release kinetics of the drug from the drug release material, although the drug release material may provide the rate-limiting control in certain embodiments, particularly for sustained release. Both the encapsulating lens material and the polymer of the drug release material may be adjusted, for example as described herein, to obtain the desired release of the at least one drug from the device. In one embodiment, the controlled release of the at least one drug from the contact lens is substantially zero-order. In certain embodiments, the contact lens provides substantially zero-order release of the at least one drug for at least 16 hours, at least 24 hours, at least 72 hours, at least 168 hours, at least 336 hours, at least 720 hours, at least 1440 hours, at least 2160 hours, at least 2400 hours, at least 2880 hours, at least 3600 hours, at least 4800 hours, at least 7200 hours, at least 9600 hours, or even longer. In other embodiments, the contact lens provides release of the at least one drug at therapeutically effective amounts for at least 168 hours, at least 336 hours, at least 720 hours, at least 1440 hours, at least 2160 hours, at least 2400 hours, at least 2880 hours, at least 3600 hours, at least 4800 hours, at least 7200 hours, at least 9600 hours, or even longer.

As used herein, the period of time in which a device releases a drug refers to the period of time in which the device is releasing a drug in a subject or in an environment that mimics the environment in a subject. As a non-limiting example, release of a drug by a device for a 24 hour period of time may be achieved by a subject wearing a contact lens continuously for 24 hours or intermittently for a total period of 24 hours (e.g., by wearing a contact lens for 1 hour per day for 24 days). Thus, when a subject wears a contact lens intermittently, the period of time refers to the time in which the subject is wearing the contact lens. The period of time may also include any time in which the contact lens is not being worn by a subject if the contact lens is in an environment in which drug is released. For example, a subject may wear a contact lens for a period of time during a day and store the contact lens in a storage solution for the remaining hours in the day. If the contact lens releases the drug during the period of time in which the contact lens is not being worn by the subject (e.g., when the contact lens is stored in a storage solution), then the time during which the contact lens is not being worn by the subject would be included when calculating the total period of time that the drug is released. However, if the rate of drug release by the contact lens when not being worn by a subject is different then the rate of drug release when the contact lens is worn by a subject, then the period of time in which a drug is released by the device when not being worn by a subject should be mathematically converted to an equivalent period of time that is based on the rate of drug release by a device when the device is worn by a subject. One of ordinary skill in the art could easily measure the rate of drug release by a device in an environment outside of a subject using methods known in the art. Furthermore, given the period of time that a device releases a drug in an environment outside of a subject and the rate at which the drug is released by the device, one of ordinary skill in the art could easily convert the period of time that the device releases the drug in an environment outside of a subject to an equivalent period of time expressed in terms of the rate of drug release by the device in a subject. These periods of time would then be added to determine the total period of time at which a drug is released at a particular rate. As a non-limiting example, if a device releases a drug in a subject at a rate of 1 microgram per hour for 2 hours, and releases the drug when not in a subject at a rate of 0.1 micrograms per hour for 10 hours, then the period of time in which a drug is released by the device would be 3 hours (i.e., 2 hours of 1 microgram per hour release plus 1 hour of an equivalent 1 microgram per hour).

When not in a subject, a device may be essentially prevented from releasing the at least one drug. When not in a subject, a device may release the at least one drug slower than when the device is in a subject. When not in a subject, a device may release the at least one drug faster than when the device is in a subject. Those of ordinary skill in the art will be able through routine experimentation to identify such conditions. For example, a device containing at least one drug may be kept in an essentially dry environment or may be kept in a solution saturated with the at least one drug in order to essentially prevent the at least one drug from being released.

Release of drug from the contact lens device may be controlled, in part, by the composition of the polymer in the drug release material. For example, increasing or decreasing the rate of release of the drug may be accomplished by altering the polymer. If the polymer is a co-polymer, such alteration may include changing the ratio of the monomers in the copolymer. In an exemplary embodiment, the polymer in the drug release material is PLGA. Increasing the ratio of lactide to glycolide generally will slow the release of the drug from the drug release material. To illustrate, polylactic acid, which contains no glycolide, may provide the slowest release system of this embodiment, whereas polyglycolic acid, which contains no lactide, may provide the fastest release system of this embodiment.

In addition or in the alternative, release of drug from the contact lens device may be controlled, in part, by the selection of the ratio of polymer to drug in the drug release material. While maintaining a constant mass of polymer, the amount of the drug in the drug release material may be reduced so that drug release materials with polymer to drug ratios of 1:2, 1:4, 1:8, 1:16; 1:32; 1:64; 1:128; 1:256; 1:512; or any other desirable ratio may be obtained. If a higher ratio of polymer is needed to attain the desired release of the drug, the potency of the drug may be adjusted. Generally, increasing the potency of the drug decreases the mass of the drug payload that must be incorporated into the drug release material. Furthermore, increasing the potency of the drug may reduce the footprint of the drug release material within the device, thereby enhancing flexibility, oxygen permeability, or cosmesis.

In some embodiments, the contact lens may contain at least 0.1 micrograms of drug, at least 1 microgram of a drug, at least 10 micrograms of a drug, at least 50 micrograms of a drug, at least 100 micrograms of a drug, at least 500 micrograms of a drug, at least 1 mg of a drug, at least 5 mg of a drug, at least 10 mg of a drug, at least 20 mg of a drug, at least 50 mg of a drug, at least 100 mg of a drug, or even more.

The rate of drug release from the device may be altered by changing the polymer concentration in the film. In one aspect, this concentration may be adjusted by altering the solvent casting procedure as described herein. The rate of drug release from the device also may be altered by casting multiple polymer-drug layers of different compositions. In one such embodiment, a lower layer may be cast with a low drug:polymer ratio, a middle layer cast with a high drug:polymer ratio, and an upper layer cast with a low drug:polymer ratio. In such an embodiment, the film would contain a high total amount of drug while maintaining a low surface permeability for drug release to prolong the release period. In another embodiment, different polymers with different solubilities may be used such that the casting of each subsequent layer has no significant effect on the preceding layer(s). In one specific embodiment, different polymers may be used to prepare the different layers. In another embodiment, the relative thicknesses of the layers can be altered to change the rate of drug release.

In some embodiments, the rate of drug release from the contact lens is at least 0.001 micrograms per hour, at least 0.005 micrograms per hour, at least 0.01 micrograms per hour, at least 0.05 micrograms per hour, at least 0.1 micrograms per hour, at least 0.5 micrograms per hour, at least 1 microgram per hour, at least 5 micrograms per hour, at least 10 micrograms per hour, at least 20 micrograms per hour, at least 50 micrograms per hour, at least 100 micrograms per hour, at least 500 micrograms per hour, at least 1 mg per hour, at least 5 mg per hour, or even more. It should be understood that a contact lens may release a drug at any these rates even if releasing the drug for less than 1 hour. As a non-limiting example, a contact lens may be worn by a subject for less than 1 hour yet still release a drug at a rate measured in terms of units of drug released per hour.

As described hereinabove, the drug release material may be structured in multiple layers or comprise a coating. The coating on the drug release material may be tailored to slow initial drug release. This effect may be achieved by sequentially applying one or more layers of polymer solution on top of the initial drug release material. In one embodiment, a multi-layered film may be created by using sequential evaporation. Multi-layered films may be created with a 1:2 ratio of drug to polymer in the middle layer and with 1:128, 1:256, and 1:512 ratios of drug to polymer on the outside layers. In one embodiment, a three-layered drug release material may be produced that has a top and bottom layer made of pure PLGA and a middle layer of 1:2 ratio of drug to polymer. In another embodiment, additional polymeric layers of varying thickness may be added in order to achieve the desired release of the drug. In some embodiments, the layers may be formed from non-polymeric materials.

In one embodiment, the hydrogel may be altered to influence the release of the drug from the device. In some embodiments, the hydrogel at least partly modulates the release of drugs from the device. In one aspect, the hydrogel may be made more hydrophobic in order to alter the release of the drug from the device. The hydrogel material may be co-polymerized with a small percentage of hydrophobic acrylates such as 1,3-butylene glycol diacrylate, isooctyl acrylate, and lauryl acrylate. Alternately, monomers with specific or non-specific affinities to the drug may be co-polymerized into the hydrogel to slow the release of the drug from the device. The release of drugs with cationic functional groups, such as timolol, may be slowed by the presence of acid groups in the hydrogel. In one embodiment, an acidic monomer such as (but not limited to) acrylic acid, methacrylic acid, fumaric acid, vinylacetic acid, itaconic acid, or maleic acid may be co-polymerized into the hydrogel.

In another embodiment, multi-functional cross-linkers, such as trimethylolpropane triacrylate, are used to create tighter junctions within the hydrogel material to prolong drug release. If the release is too slow, more hydrophilic monomers may be co-polymerized into the hydrogel. These materials may include hydrophilic, neutral acrylates such as 2-(2-ethoxyethoxy)ethyl acrylate) or vinyl pyrrolidone, and ionic monomers such as acrylic acid or betaine-containing zwitterionic methacrylates.

The contact lens device optionally may provide release of the at least one drug at a greater rate from the surface of the contact lens which contacts the patient's eye than from the opposing surface of the contact lens. Such directed drug release functionality can be designed into the device structure and/or composition. For example, (i) the lens material may comprise micro-perforations adjacent the drug release material at the side of the contact lens for contacting the cornea, (ii) the lens material adjacent the drug release material at the side of the contact lens for contacting the cornea may be thinner than the lens material adjacent the drug release material at the opposed side of the contact lens, (iii) the lens material adjacent the drug release material at the side of the contact lens for contacting the cornea may be more water permeable than the lens material adjacent the drug release material at the opposed side of the contact lens, (iv) the drug release material may be biased to release the drug toward the eye, or (v) any combination of (i) to (iv).

In one exemplary embodiment, the polymer of the drug release material comprises poly(lactic-co-glycolic) acid and the lens material comprises polyhydroxyethylmethacrylate. In another embodiment, the lens material is optically transparent along the optical axis and the drug release material comprises an aperture about the optical axis of the contact lens.

In another aspect, the device is provided in a kit, or packaged, form suitable for shipment and storage of the manufactured device prior to its use with a patient. For example, one or more contact lens drug delivery devices can be provided as a packaged medical device. For example, the contact lens may be stored in essentially any suitable packaging material, container, or other apparatus known in the art, which is capable of maintaining the contact lens devices at appropriate conditions (e.g., sterile conditions, maintained in wet or dry form as specified). In one embodiment, the packaged medical device includes one or more of the drug-eluting contact lens described herein and a packaging container. In one embodiment, the packaging container comprises a contact lens and a solution (saturated or not saturated) of drug which is the same drug as the drug in the drug-containing polymer film of the drug-eluting contact lens. In one embodiment, the packaging container comprises an aqueous solution, such as a saline solution. In another embodiment, the packaging container is capable of maintaining the drug-eluting contact lens in a dry, lyophilized state. In yet another embodiment, the packaging container is sealed with some humidity or even essentially 100% humidity and capable of maintaining the drug-eluting contact lens in a partially dry state, to minimize drug efflux from the lens device during storage and which may be helpful to decrease the pre-soak time required before application to the eye, to achieve the designed kinetics. In some embodiments, the contact lens device may be packaged in a container and be separated from a solution by a barrier, whereby the barrier may be broken to allow the solution to contact the lens prior to use.

In another aspect, a method is provided for making a contact lens drug delivery device. In one embodiment, the method includes forming a drug release material, and then encapsulating the drug release material within a lens material in the shape of a lens.

The drug release material of the device may be prepared by methods known in the art for forming biocompatible composites. In one embodiment, the drug release material is prepared by a solvent casting. In another embodiment, the drug release material may be prepared by a spin coating method or other methods known in the art. For example, the drug release material may be prepared by spin coating a mixture of the drug release material and a solvent onto an essentially dry lens material. In another embodiment, the drug release material may be prepared using a spray-drying technique. In some cases, the drug release material may be prepared using vapor deposition.

In yet another embodiment, the drug release material may be prepared by pressing a mixture of solid drug and/or release agent in a mold. The mold may or may not be lens-shaped. In another embodiment, the drug release material may be formed by solvent casting and subsequently pressed in a mold so that the drug release material adopts a curved shape (e.g., resembling a contact lens). In some cases, a drug release material having a curved shaped (e.g., resembling a contact lens) may be formed by placing a mixture containing a drug, release agent, and suitable solvent into a curved mold and rotating the mold during evaporation of the solvent. In still another embodiment, microparticles and/or nanoparticles of a drug may be fused together to form the drug release material.

A drug release material containing a plurality of layers may be formed using solvent casting, for example, by using different solvents. In some embodiments, a plurality of methods may be used to form the plurality of layers. For example, a first layer may be formed using a first method, and a second layer may be formed using a second method different from the first method.

In an embodiment in which the drug release material is made by solvent casting or using suspended drug powders instead of dissolved drug, the drug release material generally is at least 1 μm in thickness. In an embodiment in which spin coating is used to make the drug release material directly on top of a substrate of lens material, spin coating a solution in which the drug is dissolved in the polymer solution, film thicknesses on the order of 50-100 nm, at least, may be achieved.

In one embodiment, the drug release material is made by a solvent casting method. In one particular embodiment, the step of forming the drug release material may include the steps of (i) dissolving the at least one polymer in a solvent to form a polymer solution; (ii) combining the at least one drug with the polymer solution, e.g., by mixing, to form a drug-polymer solution or a drug-polymer suspension; and (iii) drying the drug-polymer solution or the drug-polymer suspension to evaporate the solvent, thereby forming the drug release material. Optionally, the cast drug release material may further be lyophilized to remove residual solvent from the drug release material before the drug release material is encapsulated.

A variety of solvents may be used in the solvent casting process in order to successfully fabricate the drug release material, with the polymer's solubility in the solvent selected being a significant consideration. Representative examples of suitable solvents that may be used in the solvent-casting process include ethanol, methanol, isopropanol, methylene chloride, ethyl acetate, acetone, or combinations thereof. In one embodiment, a co-solvent system is used in the production of the drug release material. A co-solvent system may be designed that dissolves both the drug and the polymer, which may result in a more uniform distribution (e.g., distribution on a molecular level) of drug throughout the polymer in the drug release material. Imaging techniques known in the art (SEM, TEM, optical imaging, confocal microscopy, etc.) may be used to confirm uniform distribution of the drug throughout the drug release material. In one embodiment, PLGA is dissolved in a solvent comprised of a 50:50 ratio of one of the following solvent pairs: ethyl acetate and methylene chloride; ethyl acetate and chloroform; and methylene chloride and chloroform. In another embodiment, PLLA may be dissolved in one of the following solvent pairs: methylchloride and chloroform, methylchloride and hexafluoro-2-propoanol (HFIP); and chloroform and HFIP. Regardless of the co-solvent, the same solvent casting techniques described herein may be used to fabricate the drug release material.

In another embodiment, the drug release material is made by a process that includes pressing a mixed powder of drug and/or polymer into a mold, which may be lens shaped. The pressing may be done with or without application of additional heat. The preparation optionally may include a lathing step subsequent to the molding.

The step of encapsulation may include, in one embodiment, (i) providing an encapsulation material in the form of a fluid which comprises the lens material or a polymeric precursor thereto; and (ii) solidifying the lens material or polymerizing the polymeric precursor disposed around the drug release material, thereby encapsulating it. Encapsulation requires forming a continuous matrix around the drug release material by polymerization, evaporation, etc., optionally with the aid of heat and/or pressure. In some embodiments, the step of solidifying the lens material or polymerizing the polymeric precursor may be performed in a mold corresponding to the shape/dimensions of the contact lens.

In one embodiment, a contact lens may be constructed as follows. A lens material may be lathed into a desired curved shape (e.g., an appropriate base curve). A drug release material may be placed onto the concave side of the lens material, for example, by contacting the concave side of the lens material with a preformed drug release material and/or by forming the drug release material within the concave region of the lens material using a method as described above. The drug release material may then be covered by lens material to encapsulate the drug release material. The lens material-drug release material-lens material structure may then be lathed on the anterior and posterior surfaces to form a contact lens.

In another embodiment, a contact lens may be constructed by providing a first lens material layer having a curved structure, depositing a drug release material on to the convex surface of the lens material, and joining a second lens material layer onto the drug release material and first lens material layer, thereby forming a contact lens having a first lens material layer and a second lens material layer with a drug release material disposed between the first lens material layer and a second lens material layer. In some embodiments, the iris portion of the contact lens comprises mica.

A lens material in liquid form may be pretreated prior to use in fabricating a device. For example, the pH of the liquid lens material may be adjusted to be neutral, acidic, or basic. In another example, the liquid lens material may be prepolymerized to form a partially polymerized material. In yet another example, the salinity and/or osmolarity of the liquid lens material may be adjusted. In embodiments where the liquid lens material is polymerized using light, the concentration of a photoinitiator and/or the intensity of the light source used for curing may be adjusted to increase or decrease the polymerization time. Polymerization of a liquid lens material may also carried out in an essentially oxygen-free environment.

In some cases, the drug release material and the lens material may adhere. Adhesion between these materials may be improved by a variety of methods. For example, at least a portion of the surface of the drug release material may be made uneven (i.e., rough). An uneven portion may be introduced by forming the drug release material in a mold, where at least a portion of the surface of the mold is uneven. A portion of the surface of the drug release material may also be subjected to mechanical abrasion. In another embodiment, indentations (e.g., holes or channels) may be formed in the drug release material. In one embodiment, the drug release material and/or lens material may be chemically modified to increase the adhesion between the drug release material and the lens material. For example, the drug release material and/or lens material may be subjected to plasma treatment, covalent modification with a functional group, or the like to increase the hydrophilicity of the material. In another embodiment, a polymer may be adsorbed to the drug release material and/or lens material to increase the adhesion between the drug release material and lens material.

In some cases, adhesion between the drug release material and the lens material may be decreased. For example, it may be desirable to increase the lubricity between the drug release material and the lens material to facilitate movement between the two materials. In some embodiments the hydrophobicity of drug release material and/or the lens material is increased, for example, by adsorbing a hydrophobic polymer to one or both materials, or covalently modifying one or both materials.

It may be desirable to have the contact lens remain in a selected orientation when applied onto the cornea. For example, this may facilitate cosmesis or enhance the direction or eye region to which the drug is administered, e.g., by allowing the drug release material to remain in a selected orientation on the eye. In one embodiment, the contact lens device can be stabilized from rotation by incorporating a prism ballast or tapered thin zones into the device during the encapsulation process.

Typically, the position of the drug release material within the lens material becomes fixed during the encapsulation process. The drug release material may be located in various lateral positions (e.g., position relative to the optical axis) and depth positions (e.g., position relative to the cornea) within the lens material of the device. Generally, however, the drug-polymer is positioned outside of the optical axis in those embodiments where the drug release material is not substantially optically transparent. If, on the other hand, the drug release material is substantially optically transparent, then it may be positioned in any location within the lens material.

In one embodiment, the contact lens device has a single drug release material. The single drug release material may have a variety of different shapes. In one embodiment, the single drug release material is ring shaped with the aperture being substantially coaxial with optical axis. In another embodiment, the single drug polymer film has arc shape. The arc shape may be an arch, a crescent, or a segment of a circle. The shape of the drug release material can be formed by using a mold of the desired shape or by using a mold of essentially any larger shape to make a temporary film and then cutting the temporary film into the final, desired shape. The precise cutting may be carried out for example using mechanical cutting equipment known in the art or by using laser cutting instruments known in the art.

In one embodiment, the drug release material comprises a plurality of perforations. For example, perforations may be microperforations. The microperforations may be located throughout a portion of the drug release material or throughout all of the drug release material. Without wishing to be bound by any theory, the microperforations may serve to increase drug release and provide a pathway for oxygen transport through the drug release material to the cornea. Oxygen transport can, in some embodiments, be sufficiently high for the contact lens drug delivery device to be suitable for long term wear by the patient.

In an alternative embodiment, the lens device may comprise two or more polymer drug films. The two or more films may be in essentially any shape and in any position relative to one another within the lens material.

If the drug release material has an aperture, it optionally may be positioned within the lens material so that the aperture corresponds with the patient's optical axis. In one embodiment, the drug release material is positioned within the lens material and the device sized so that when the contact lens device is worn, the drug release material is concealed by one or both of the patient's eyelids.

In an optional embodiment, the contact lens device may be provided in a colored form, for example by (i) incorporating colorant particles into the lens material and/or drug release material, (ii) coating the lens material and/the drug polymer film with a colored film similar to a conventional cosmetic contact lens, or (iii) a combination of (i) and (ii).

The device may be manufactured in a manner that promotes the release of the drug toward or away from the cornea or sclera. In one embodiment, the device may be produced so that that the portion of the encapsulating hydrogel lens material on one side of the drug release material is thinner relative to the portion of the encapsulating hydrogel lens material on the other side of the drug release material. In another embodiment, a certain portion of the hydrogel lens material may be made more hydrophobic or hydrophilic to promote the unidirectional release of the drug from the device. Alternatively, a certain portion of the encapsulating hydrogel lens material may be made more gas soluble or gas permeable in order to promote the unidirectional release of the drug from the device. In yet another embodiment, portions of the encapsulating hydrogel lens material may be perforated in order to promote the unidirectional release of the drug from the device. Typically, the perforations are micro-perforations. Preferably, the micro-perforations are of a size that does not interfere with the patient's comfort, the overall cosmesis, or the structural integrity of the device. The perforations in the hydrogel may be produced, for example, using a "pinned hand tool", which is obtainable for example from Stewarts of America or other manufacturers. The tool may be used to create up to 1000 perforations per square inch.

In another aspect, a method is provided for administering one or more drugs to the eye of a patient in need thereof. In one embodiment, the method includes the steps of applying one of the drug-eluting contact lens devices described herein onto the patient's cornea; and then permitting the drug to be controllably released from the contact lens to the patient's eye in a therapeutically or prophylactically effective amount. In one embodiment, the controlled release of the drug from the contact lens is substantially zero-order. In one particular embodiment, the contact lens is sized so that when the lens is worn by the patient, the contact lens is disposed over the cornea and conjunctiva and at least partially under the upper or lower eyelid. In one embodiment, the lens material is sufficiently oxygen permeable to allow the contact lens to be worn by the patient continuously for the desired period of drug release, e.g., for up to 720 hours.

In various embodiments, the drug-eluting contact lens devices may provide substantially zero-order release of the drug for at least 72 hours, at least 168 hours, at least 336 hours, at least 720 hours, at least 1440 hours, at least 2160 hours, at least 2400 hours, at least 2880 hours, at least 3600 hours, at least 4800 hours, at least 7200 hours, at least 9600 hours, or even more. In other embodiments, the device may provide substantially zero-order release of the drug for up to 4000 hours, or up to 9000 hours.

In one particular embodiment and use, the contact lens device acts as a bandage contact lens. In a particular embodiment, the bandage contact lens includes a drug release material encapsulated within a hydrogel lens material, the drug release material including a drug dispersed in a polymer, wherein the contact lens, when worn by a patient on the patient's eye, provides controlled release of an effective amount of the drug to the patient for 24 to 720 hours. In various embodiments, the drug may comprise an antibiotic agent, an antifungal agent, an anesthetic agent, a non-steroid anti-inflammatory (NSAID) agent, an antihistamine or other antiallergy agent, or a combination thereof. The polymer may be biodegradable. In one embodiment, the bandage contact lens provides controlled release of an effective amount of the drug to the patient for at least 240 hours.

In one particular application, devices and method are provided for prophylaxis and/or treatment of an eye infection in a patient. In one embodiment, the method includes applying one of the contact lens devices described herein to the patient's cornea, wherein the drug release material includes at least one anti-infective agent, and then releasing (or permitting the release of) the anti-infective agent from the contact lens to the patient's eye in an effective amount for up to 720 hours. Representative examples of the duration of drug release include at least 72 hours, at least 168 hours, at least 240 hours, at least 336 hours, at least 504 hours, or even longer. In one embodiment, the release of the anti-infective agent from the contact lens is substantially zero-order. In another embodiment, the contact lens includes a second drug, such as a local anesthetic agent, for co-administration with the anti-infective agent. In one embodiment, the contact lens is applied to the eye perioperatively. In another embodiment, the contact lens is applied to the eye following trauma to the eye. In one embodiment, the applied contact lens is disposed at least partially under an eyelid of the patient. In some cases, the drug release material within the contact lens is also disposed under an eyelid of the patient.

In another aspect, the controlled release device described herein is implanted into the patient's cornea. In yet another embodiment, the device described herein may be sutured to the sclera of the patient's eye. In still another embodiment, the device may comprise an intraocular lens. Typically, but not always, this embodiment of the device comprises an optic portion and a haptics portion. An intraocular lens may be an optic lens, a haptic lens, or both an optic and haptic lens. In yet another embodiment, the device described herein may comprise a glaucoma tube. For example, the device may be a glaucoma drainage device. Examples of glaucoma drainage devices include a tube, shunt, filter, or Ahmed™ valve. In still another embodiment, the device may be a capsular tension ring, an ocular conformer, punctual plug, scleral buckle, suture, intra-stromal inlay (e.g., Intacs®), or an ocular surface therapy device (e.g., ProKera®). As described hereinabove, the structure of the drug delivery device may be altered to accommodate these and other embodiments.

In still another aspect, the drug delivery device described herein may be adapted for use in areas of the human or animal body besides the eye. Generally, the device may be used in any portion of the body that would benefit from the controlled release of a drug. The device may be inserted, sutured, or placed onto various tissue structures or into various vesicles or cavities where local controlled drug release is desired.

The device may include one or more anti-infective agents for controlled release. Non-limiting examples of suitable anti-infective agents include ciprofloxacin, moxifloxacin, galtfloxacin, vancomyacin, tobramyacin, or a combination thereof. Other known anti-infective agents may be incorporated into and released from the contact lens device. In still other embodiments, the contact lens may include a second drug, such as a steroid (e.g., corticosteroids), non-steroidal anti-inflammatory drugs (NSAIDs), local anesthetic agent, or other drug, for co-administration with the anti-infective agent. In one embodiment, a contact lens drug delivery device is provided which includes a combination of an anti-infective and a steroid. The device may be used, for example, to administer both an anti-infective and a steroid to the cornea for post-treatment of corneal surgeries. The local anesthetic agent may be an aminoamide, an aminoester, or a mixture thereof. Combinations of different aminoamides or combinations of different aminoesters are envisioned. Representative examples of possible aminoamides include lidocaine, prilocalne, mepivacaine, and ropivacaine. Representative examples of possible aminoesters include benzocaine, procaine, proparacaine, and tetracaine.

In some embodiments, plasticizers may be incorporated into the device to alter the drug release characteristics of the device. As used herein, the plasticizer is any material known in the art that can be blended with the polymer (e.g., the polymer of the drug release material) to increase its mechanical flexibility. Plasticizers may also affect the drugs' incorporation into the polymer of the drug release material and release kinetics. Any biocompatible plasticizer known in the art may be used. Examples of plasticizers include compounds of the pluronic/poloxamer non-ionic surfactant family and lipids. Particular plasticizers that may be used include Span 20, Tween 20, propylene glycol, or combinations thereof. In a specific example, sorbitan monolaurate and propylene glycol can be used in PLGA-timolol films intended for use in the inferior formex. In one, non-limiting embodiment, the drug release material of a device includes, by weight, 30% drug, 50% polymer, and 20% plasticizer. In other embodiments, more plasticizer or less plasticizer may be used. Other components may be included in the lens device, either in the lens material, the drug release material, or both, in minor amounts to impart one or more useful properties to the device.

The compositions and methods disclosed herein may be used to treat a variety of diseases and/or conditions, for example: eye infections (including, but not limited to, infections of the skin, eyelids, conjunctivae, and/or lacrimal excretory system), orbital cellulitis, dacryoadenitis, hordeolum, blepharitis, conjunctivitis, keratitis, corneal infiltrates, ulcers, endophthalmitis, panophthalmitis, viral keratitis, fungal keratitis herpes zoster ophthalmicus, viral conjunctivitis, viral retinitis, uveitis, strabismus, retinal necrosis, scleritis, mucormycosis, canaliculitis, acanthamoeba keratitis, toxoplasmosis, giardiasis, leishmanisis, malaria, helminth infection, glaucoma, etc. It should be understood that other diseases and/or conditions may be treated as well.

As described herein, a device may be configured to release an active agent. In some embodiments, a device may be loaded with an active agent. The active agent may be selected from small molecules, organic compounds, inorganic compounds, proteins, nucleic acids, and/or carbohydrates. In some cases, the active agent may be a pharmaceutical agent (e.g., a drug). In certain instances, the pharmaceutical agent may be used to treat the eye. Suitable drugs include, but are not limited to, growth factors; angiogenic agents; anti-inflammatory agents; anti-infective agents such as antibacterial agents, antiviral agents, antifungal agents, and agents that inhibit protozoan infections; antineoplastic agents; anesthetics; anti-cancer compositions; autonomic agents; steroids (e.g., corticosteroids); non-steroidal anti-inflammatory drugs (NSAIDs); antihistamines; mast-cell stabilizers; immunosuppressive agents; antimitotic agents; or other drug. In some embodiments, the active agent may be a wetting agent, surfactant, ocular demulcent, electrolyte, buffer, or preservative. In some cases, an active agent may improve a subject's comfort when wearing a contact lens device. It should be understood that an active agent need not be restricted to a particular indication.

The device may include one or more antibacterial agents for controlled release. Non-limiting examples of suitable antibacterial agents include bacitracin, chloramphenicol, ciprofloxacin, erythromycin, moxifloxacin, gatifloxacin, gentamicin, levofloxacin, sulfacetamide, polymyxin B, vancomycin, tobramycin, or a combination thereof. Other antibacterial agents may be incorporated into and released from the device.

Antiviral agents include, but are not limited to, trifluridine, vidarabine, acyclovir, valacyclovir, famciclovir, foscarnet, ganciclovir, formivirsen, and cidofovir.

Antifungal agents include, but are not limited to, amphotericin B, natamycin, fluconazole, itraconazole, ketoconazole, and miconazole.

Antiprotozoal agents include, but are not limited to, polymyxin B, neomycin, clotrimazole, miconazole, ketoconazole, propamidine, polyhexamethylene biguanide, chlorhexidine, itraconazole Anesthetic agents include, but are not limited to, an aminoamide, an aminoester, or a mixture thereof. Combinations of different aminoamides or combinations of different aminoesters are envisioned. Representative examples of possible aminoamides include lidocaine, prilocalne, mepivacaine, and ropivacaine. Representative examples of possible aminoesters include benzocaine, procaine, proparacaine, and tetracaine.

Autonomic agents include, but are not limited to, acetylcholine, carbachol, pilocarpine, physostigmine, echothiophate, atropine, scopolamine, homatropine, cyclopentolate, tropicamide, dipivefrin, epinephrine, phenylephrine, apraclonidine, brimonidine, cocaine, hydroxyamphetamine, naphazoline, tatrahydrozoline, dapiprazole, betaxolol, carteolol, levobunolol, metipranolol, and timolol.

Anti-inflammatory agents include, but are not limited to, any known non-steroidal anti-inflammatory agent, and any known steroidal anti-inflammatory agent. Non-limiting examples include glucocorticoids (e.g., dexamethasone, prednisolone, fluorometholone, loteprednol, medrysone, and rimexolone) and NSAIDS (e.g., diclofenac, flurbiprofen, ketorolac, bromfenac, and nepafenac).

Antihistamines include, but are not limited to, pheniramine, antazoline, naphazoline, emedastine, levocabastine, and cromolyn.

Mast-cell stabilizers include, but are not limited to, lodoxamide, pemirolast, nedocromil, olopatadine, ketotifen, azelastine, and epinastine.

Antimicrobial agents include antibiotics (e.g. antibacterial), antiviral agents, antifungal agents, and anti-protozoan agents.

Antineoplastic agents include, but are not limited to, those which are suitable for treating tumors of the eye and its adnexa including cancer chemotherapeutic agents, a variety of which are well known in the art.

In some embodiments, a device may be loaded with an active agent by soaking the device in a solution containing the active agent. Generally, the loading of active agent can be increased by increasing the concentration of the active agent in the soaking solution and/or increasing the contact time between the device and the soaking solution. An active agent may also adsorb onto the surface of the device. The association of an active agent with a device may result from non-covalent interactions. Alternatively, an active agent may be reacted with a release agent and/or lens material to form a covalent bond. As known to those in the art, a covalent bond may be chosen such that under certain conditions (i.e., physiological conditions), the bond may break thereby releasing the active agent. Depending on the ratio of the active agent to the release agent and/or the lens material, the nature of the particular release agent and/or lens material employed, and the type of association between the active agent and the release agent and/or lens material, the rate of release of the active agent can be controlled.

In some embodiments, a virus and/or cell may be delivered using the device. The device may be configured such that the virus and/or cell can be released in sustained fashion. In some cases, a virus may be used for gene delivery. Gene delivery may be beneficial, for example, for transforming non-proliferative cells into proliferative cells (i.e., for regeneration of eye tissue). A cell may be used, in some instances, as an active agent factory. For example, a cell (i.e., a stem cell) may secrete a growth factor or other agent that has therapeutic value. By placing such cells proximate the eye, these cells may continuously generate and deliver a therapeutic.

The drug release materials and/or lens materials described herein may be used in "pharmaceutical compositions" or "pharmaceutically acceptable" compositions, which comprise a therapeutically effective amount of an active agent associated with one or more of the drug release materials and/or lens materials described herein, formulated together with one or more pharmaceutically acceptable carriers, additives, and/or diluents. The pharmaceutical compositions described herein may be useful for diagnosing, preventing, treating or managing a disease or bodily condition including eye conditions. In some cases, a composition includes a drug release material encapsulated in a hydrogel and placed proximate the eye.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid, gel or solid filler, diluent, excipient, or solvent encapsulating material, involved in carrying or transporting the subject compound, e.g., from a device or from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The amount of active agent which can be combined with a polymer or other carrier material to produce a single dosage form will vary depending upon the host being treated, and the particular mode of administration. The amount of active agent that can be combined with a polymer or other carrier material to produce a single dosage form will generally be that amount of the compound which produces a therapeutic effect. Generally, this amount will range from about 1% to about 99% of active ingredient, from about 5% to about 70%, or from about 10% to about 30%. It should be understood that ranges outside these ranges may be used as well.

Drug release materials described herein suitable for encapsulation may be formulated as a solution, dispersion, or a suspension in an aqueous or non-aqueous liquid, as an emulsion or microemulsion (e.g., an oil-in-water or water-in-oil liquid emulsion), or as an elixir or syrup, or as pastilles (using an inert base, such as gelatin and glycerin, or sucrose and acacia), each containing a predetermined amount of a polymer or non-polymeric excipient described herein, and optionally including an active ingredient.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A liquid dosage form may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to an active agent, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

These compositions and devices described herein may also contain adjuvants such as preservatives, wetting agents, emulsifying agents, lubricating agents and dispersing agents. Prevention of the action of microorganisms upon the devices may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions.

Delivery systems suitable for use with devices described herein include time-release, delayed release, sustained release, or controlled release delivery systems. Many types of release delivery systems are available and known to those of ordinary skill in the art. Specific examples include, but are not limited to, erosional systems in which the composition is contained in a form within a matrix, or diffusional systems in which an active component controls the release rate. The compositions may be as, for example, particles (e.g., microparticles, microspheres, nanoparticles), hydrogels, polymeric reservoirs, or combinations thereof. In some embodiments, the system may allow sustained or controlled release of an active agent to occur, for example, through control of the diffusion or erosion/degradation rate of the formulation or particle. The devices described herein can also be combined (e.g., contained) with delivery devices such as syringes, catheters, tubes, and implantable devices.

When the devices described herein are administered as pharmaceuticals, to humans and animals, they can be given per se or as a pharmaceutical composition containing, for example, about 0.1% to about 99.5%, about 0.5% to about 90%, or the like, of drug release material in combination with a pharmaceutically acceptable carrier.

The agents described herein may be given in dosages, e.g., at the maximum amount while avoiding or minimizing any potentially detrimental side effects. The agents can be administered in effective amounts, alone or in a combinations with other compounds. For example, when treating cancer, a composition may include a cocktail of compounds that can be used to treat cancer.

The phrase "therapeutically effective amount" as used herein means that amount of a material or composition which is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

In some embodiments, the effective amount of any drug release described herein may be from about 1 ng/kg of body weight to about 10 mg/kg of body weight, and the frequency of administration may range from once a day to a once a month basis, to an as-needed basis. However, other dosage amounts and frequencies also may be used as the invention is not limited in this respect. A subject may be administered devices described herein in an amount effective to treat one or more diseases or bodily conditions described herein.

The effective amounts will depend on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

The selected dosage level can also depend upon a variety of factors including the activity of the particular inventive structure employed, the route of administration, the time of administration, the rate of excretion or metabolism of the materials or active agents being employed, the duration of the treatment, other drugs, compounds and/or materials used in combination with the particular material employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the agents described herein employed in the pharmaceutical composition at levels lower than that required to achieve the desired therapeutic effect and then gradually increasing the dosage until the desired effect is achieved.

In some embodiments, a device or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a device or pharmaceutical composition repeatedly over the life of the subject. For example, chronic treatments may involve regular administrations, for example one or more times a week, or one or more times a month.

While it is possible for a device described herein to be administered alone, it may be administered as a pharmaceutical composition as described above. Any of the above-mentioned compositions useful for diagnosing, preventing, treating, or managing a disease or bodily condition may be packaged in kits, optionally including instructions for use of the composition. That is, the kit can include a description of use of the composition for participation in any disease or bodily condition, The kits can further include a description of use of the compositions as discussed herein. Instructions also may be provided for administering the composition by any suitable technique.

The kits described herein may also contain one or more containers, which can contain components such as the devices and/or active agents as described herein. The kits also may contain instructions for preparing and/or administrating the devices. The kits also can include other containers with one or more solvents, surfactants, preservatives, and/or diluents (e.g., normal saline (0.9% NaCl), or 5% dextrose) as well as containers for preparing and/or administering the devices to the patient in need of such treatment.

The compositions of the kit may be provided as any suitable form, for example, essentially dry or at least partially hydrated. When essentially dry, the composition may be hydrated by the addition of a suitable solution, which may also be provided. In embodiments where at least partially hydrated forms of the composition are used, the liquid form may be concentrated or ready to use. The kit, in one set of embodiments, may comprise one or more containers such as vials, tubes, syringes, and the like, each of the containers comprising one or more of the elements to be used in the method. For example, one of the containers may contain a device. Additionally, the kit may include containers for other components, for example, solutions to be mixed with the device prior to administration.

As used herein, a "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, the devices are directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition.

EXAMPLES

Various embodiments are further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and the scope of the appended claims.

The materials used in the following examples were obtained from a variety of suppliers. Poly(lactic-co-glycolic acid)s (PLGAs) were obtained from Lakeshore Biomaterials (Birmingham, Ala.). The PLGAs included samples with molecular weights of 118 kDa (65:35; 65% lactic acid and 35% glycolic acid) and 18 kDa (50:50). Cipro™ I.V. (ciprofloxacin 0.2% ready-for-use infusion solutions in 5% dextrose injection) was purchased from Bayer Pharmaceutical Corporation (West Haven, Conn.). Irgacure 3959 was obtained from Ciba Specialty Chemicals Corporation (Tarrytown, N.Y.). Medium grade acrylic resin was obtained from the London Resin Company (Reading, Berkshire, England). Ciprofloxacin powder, fluorescein, HEMA and all the other reagents were purchased from Sigma Aldrich (St. Louis, Mo.).

Clinical ocular-related *Staphylococcus aureus* strains were obtained from the Massachusetts Eye and Ear Infirmary (MEEI) Clinical Laboratory and recovered from human cornea, eyelid and canaliculus infections; the minimal inhibitory concentrations for all bacterial isolates were determined by standard methods promulgated by the National Committee for Clinical Laboratory Standards (NCCLS). MEEI-IB01 is a ciprofloxacin-resistant keratitis strain (minimum inhibitory concentration [MIC]>2 µg/ml). MEEI-IB03, MEEI-IB012, and MEET-IB013 are ciprofloxacin-sensitive (MIC<1 µg/ml) strains.

Example 1

Fabrication of Drug Release Materials

To create a drug release material, PLGA was dissolved in 15 mL of ethyl acetate. Fluorescein was added to the solution and mixed to form a suspension inside the PLGA solution. Films were created with 118 kDa ("high") and 18 kDa ("low") molecular weight PLGA polymers and various ratios of PLGA to fluorescein (Table 1). The suspension was poured into a Teflon well. The ethyl acetate was removed by evaporation in a fume hood with laminar air flow overnight, then lyophilized for 48 hours. In this particular aspect, rings with a 14 mm outer diameter and a 5 mm central aperture were punched out of the fluorescein-PLGA film.

Fluorescein-containing PLGA films were created with the same mass of fluorescein and differing masses of PLGA, differing ratios of lactide to glycolide, and PLGA polymers of high and low molecular weights.

TABLE 1

Composition of Lens Prototypes

| Fluorescein:PLGA ratio | Fluorescein (mg) | PLGA (mg) | L:G ratio* | PLGA Mol. Wt. |
|---|---|---|---|---|
| 2:1 | 20 | 10 | 65:35 | 118 kDa (high) |
| 1:1 | 20 | 20 | 65:35 | 118 kDa (high) |
| 1:2 | 20 | 40 | 65:35 | 118 kDa (high) |
| 1:1 | 20 | 20 | 50:50 | 118 kDa (high) |
| 1:1 | 20 | 20 | 50:50 | 18 kDa (low) |

*ratio of lactide to glycolide in PLGA

Ciprofloxacin films were also created by solvent-casting as described above, using PGLA 65:35 (118 kDa molecular weight) and a 1:1 ratio of medication to PLGA (20 mg of ciprofloxacin and 20 mg of PLGA).

Example 2

Encapsulating the Drug Release Material with pHEMA

The drug release materials of Example 1 each were encapsulated with pHEMA using an ultraviolet (UV) polymerization process, as follows. 11.6 mL of the monomer HEMA and 44 µL of the crossslinker ethyleneglycol dimethacrylate (EGDMA) were dissolved in 8.6 mL of deionized water. 100 µL of 0.1 g/mL Irgacure 2959 photo-initiator in dimethyl sulfoxide was then added and the resulting solution was degassed under nitrogen for 40 minutes. 160 µL of that solution was transferred into a 100 µm deep cylindrical rubber mold (16 mm diameter), covered with a glass slide, and placed in a nitrogen filled plastic bag. The solution was then polymerized with a 305 nm UV lamp for 60 minutes to form the bottom pHEMA portion of the composite contact lens.

The drug release material was manually pressed onto the dried pHEMA gel and placed in a custom-made cylindrical rubber mold (450 µm deep by 16 mm in diameter). The rubber mold was then filled with the HEMA monomer photoinitiator solution and UV-polymerized. The resulting contact lens consisted of a thin drug release material encapsulated with pHEMA. This particular contact lens had a total thickness of 450 µm and a 16 mm outside diameter.

For comparison purposes, crystalline fluorescein without PLGA was also encapsulated in pHEMA. Twenty mg of fluorescein was suspended in 15 mL of ethyl acetate and poured into a cylindrical rubber mold with a central 5 mm rubber plug, which had been clamped on top of a 100 µm thick pre-formed pHEMA dehydrated gel. The ethyl acetate was allowed to evaporate overnight in a fume hood, leaving behind a thin layer of fluorescein crystals which occupied the same footprint as the drug-PLGA films prepared in the prototype lenses. The fluorescein was then encapsulated with pHEMA, as described above, and lyophilized.

FIG. 1 is a photograph of a contact lens device made according to the methods described in Examples 1 and 2. The contact lens device consists of a ciprofloxacin drug release material 1 encapsulated with pHEMA 2.

Example 3

Drug Release Studies

In order to study drug release, the contact lenses made as in Example 2 were placed inside a 50 mL centrifuge tube containing 15 mL of phosphate buffered saline (PBS) (pH=7.4). The centrifuge tube was placed in a 37° C. incubator with continuous shaking. The PBS was sampled and replaced completely at predetermined intervals. The amount of fluorescein released into the PBS media was measured using a UV/VIS spectrophotometer (Molecular Devices, Sunnyvale, Calif.) at a wavelength of 490 nm. Concentrations and masses of released fluorescein at each kinetic time point were calculated based on a calibration curve prepared with known fluorescein concentrations ($R^2>0.99$). Four individual contact lenses were tested for each formulation.

The release of fluorescein in the absence of a drug delivery device was tested by suspending 25 mg of free fluorescein powder in 15 mL of PBS. The tubes were centrifuged, and the supernatants were assayed at the same predetermined intervals as the drug delivery devices.

The mass of ciprofloxacin released into the media was quantified using high pressure liquid chromatography (HPLC) (110 series, Agilent Technologies, Palo Alto, Calif.). An Atlantis™ dC18 analytical column (4.6×250 mm; particle size 5 µm) was used with a mobile phase mixture composed of 10 mM phosphate buffer (pH 2.1) and acetonitrile. Ratios of acetonitrile to phosphate buffer were increased from 20% to 70% over 8 minutes and then returned to 20% over the next two minutes. The flow rate was set at 1 mL/min. The samples were filtered through 0.45 µm syringe filters and 20 µL of the samples were injected into the pre-equilibrated column. Ciprofloxacin concentrations were determined using a UV detector set at 275 nm and correlating the measured peak areas with those measured for a series of ciprofloxacin standards (prepared from Cipro-IV solution) freshly prepared for each HPLC run.

Figure 3A:
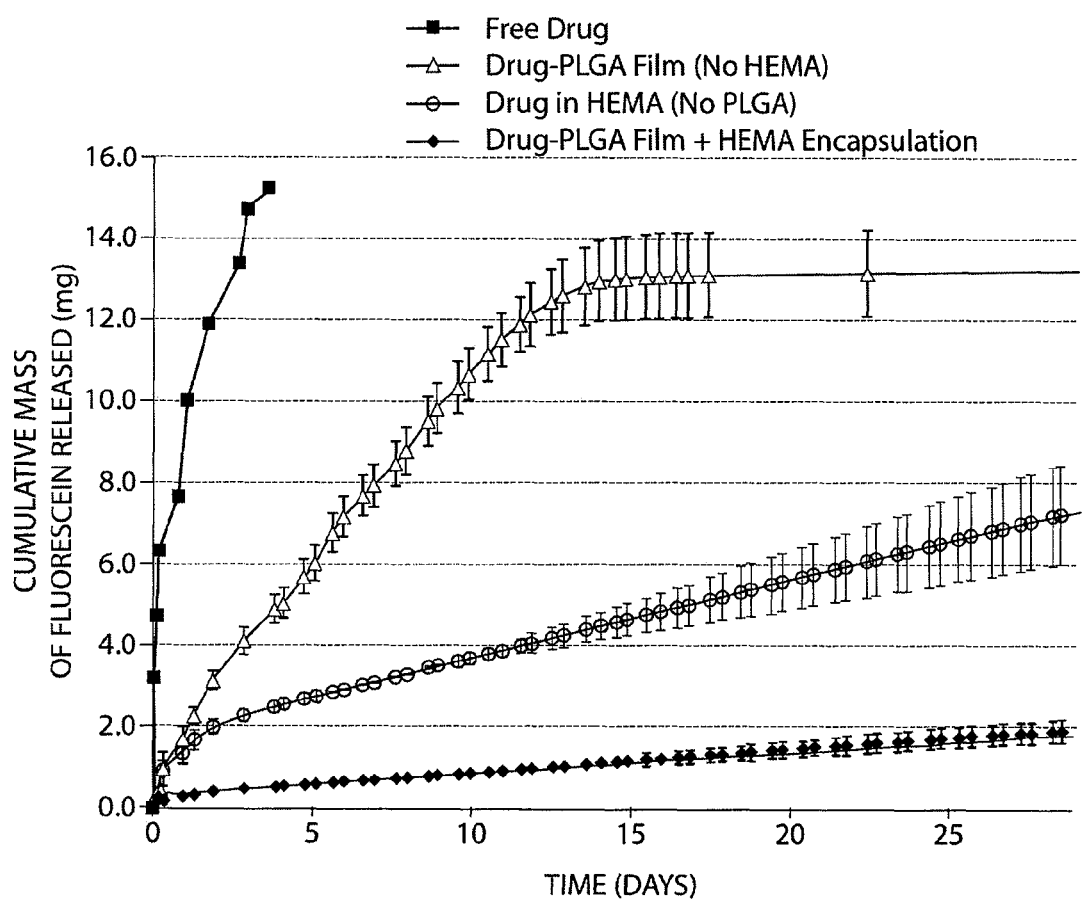
FIG. 3a is a graph illustrating the cumulative release from free fluorescein powder, fluorescein-PLGA films, and fluorescein-PLGA films encapsulated with pHEMA over 30 days. Data are means with standard deviations.

Unencapsulated fluorescein-PLGA films (PLGA 65:35, high [118 kDa] molecular weight) showed drug release with linear kinetics for 10 days, releasing 65% of the fluorescein in the film, with little release thereafter. Encapsulation of the fluorescein-PLGA films with pHEMA resulted in significantly slower and longer release kinetics, providing more than 4 weeks of release with substantially zero-order kinetics, while releasing 10% of the total fluorescein in the film (FIG. 3a). Release from both devices was significantly slower than the dissolution rate of free fluorescein powder. When the drug was encapsulated with pHEMA without a PLGA film, the release profile was slower than that from drug in the PLGA film but faster than that from drug in a PLGA film encapsulated with pHEMA. There was a greater degree of variability in fluorescein release than was observed when the drug was contained in PLGA encapsulated with pHEMA. Therefore, both the PLGA film and the pHEMA appear to be contributing factors in controlling the release of fluorescein from the prototype contact lens.

Figure 3B:
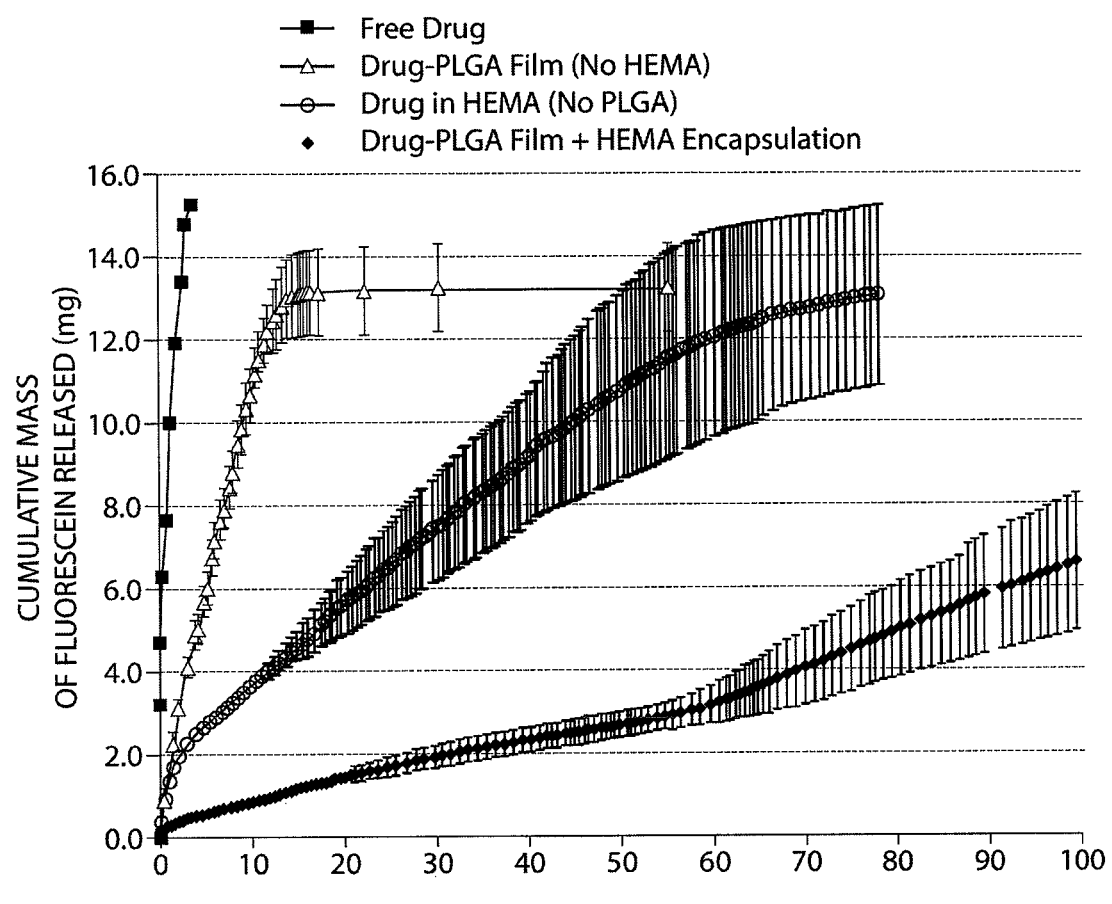
FIG. 3b is a graph illustrating the cumulative release from free fluorescein powder, fluorescein-PLGA films, and fluorescein-PLGA films encapsulated with pHEMA over 100 days. Data are means with standard deviations.

The pHEMA-encapsulated PLGA film continued to release for at least 100 days (FIG. 3b), at which time 33% of the encapsulated fluorescein had been released. This release continued to demonstrate the same substantially zero-order kinetics for 60 days, then increased to a higher, but still substantially zero-order release rate. After 100 days of release, the PLGA film encapsulated with pHEMA retained a yellow coloring, indicating that much of the fluorescein was still retained inside the prototype lens.

Figure 4:
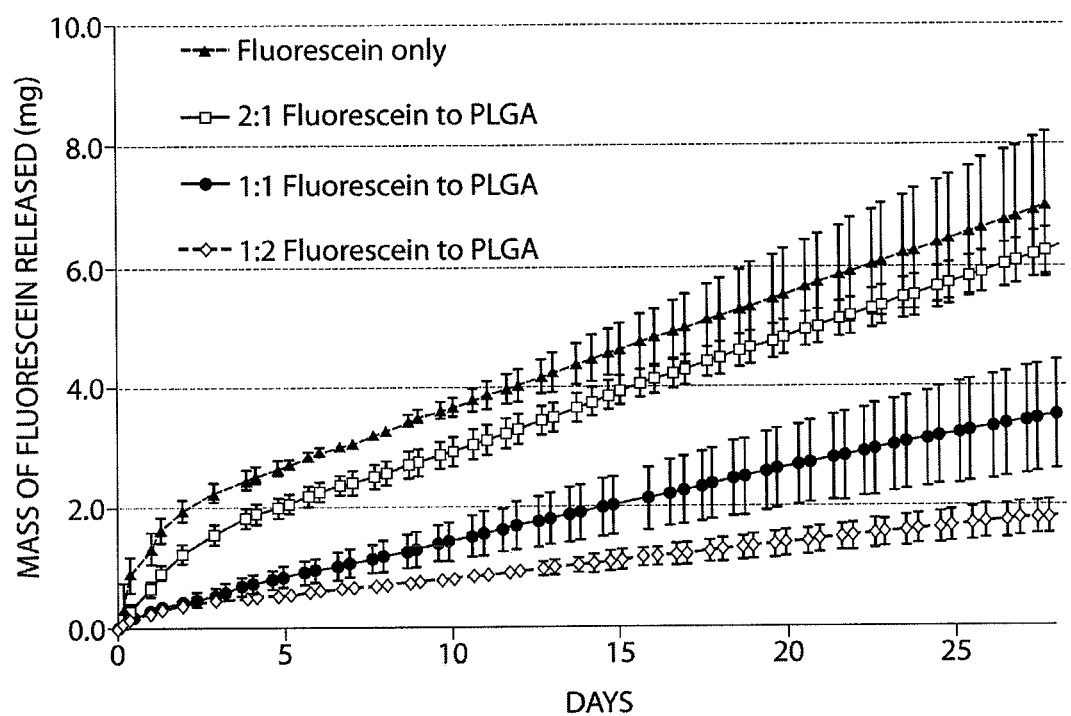
FIG. 4 is a graph illustrating the cumulative release of fluorescein encapsulated with pHEMA, without PLGA ("Fluorescein, no PLGA"), or with varying proportions of fluorescein to PLGA. The mass of fluorescein per device is constant between groups. Data are means with standard deviations.
Figure 5:
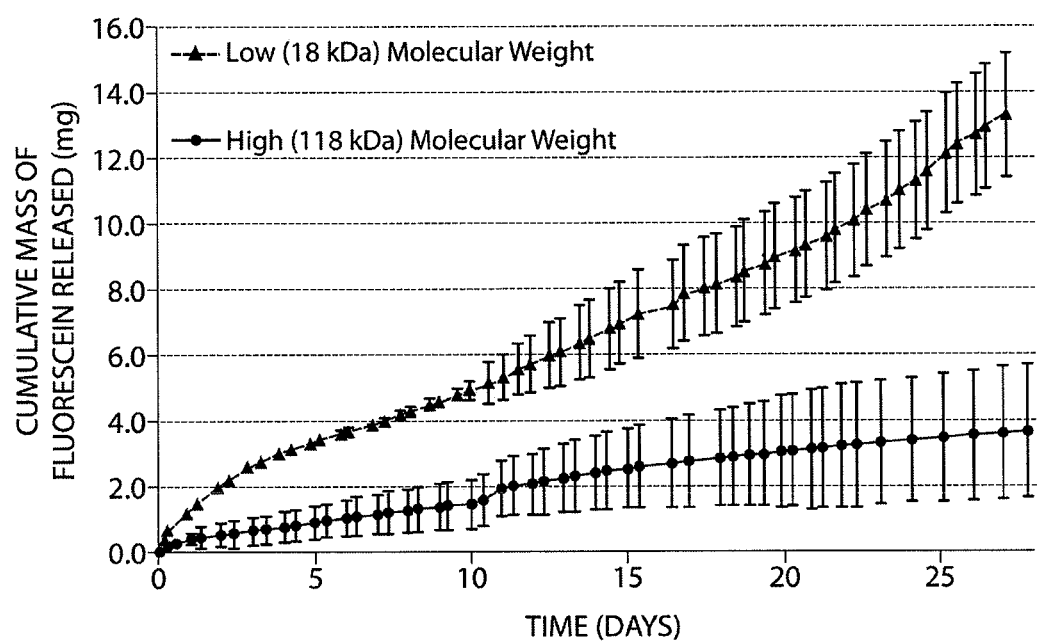
FIG. 5 is a graph illustrating the cumulative release of fluorescein from low (18 kDa) and high (118 kDa) molecular weight PLGA films encapsulated with pHEMA. Data are means with standard deviations.

Varying the ratio of PLGA to drug changed the rate of release of fluorescein from PLGA films encapsulated with pHEMA, while maintaining substantially zero-order kinetics through 4 weeks (FIG. 4). Increasing the proportion of PLGA to fluorescein (keeping the mass of fluorescein constant) slowed the release of fluorescein, as did increasing the molecular weight of the PLGA (FIG. 5). Both modifications maintained near zero-order release kinetics.

Figure 6:
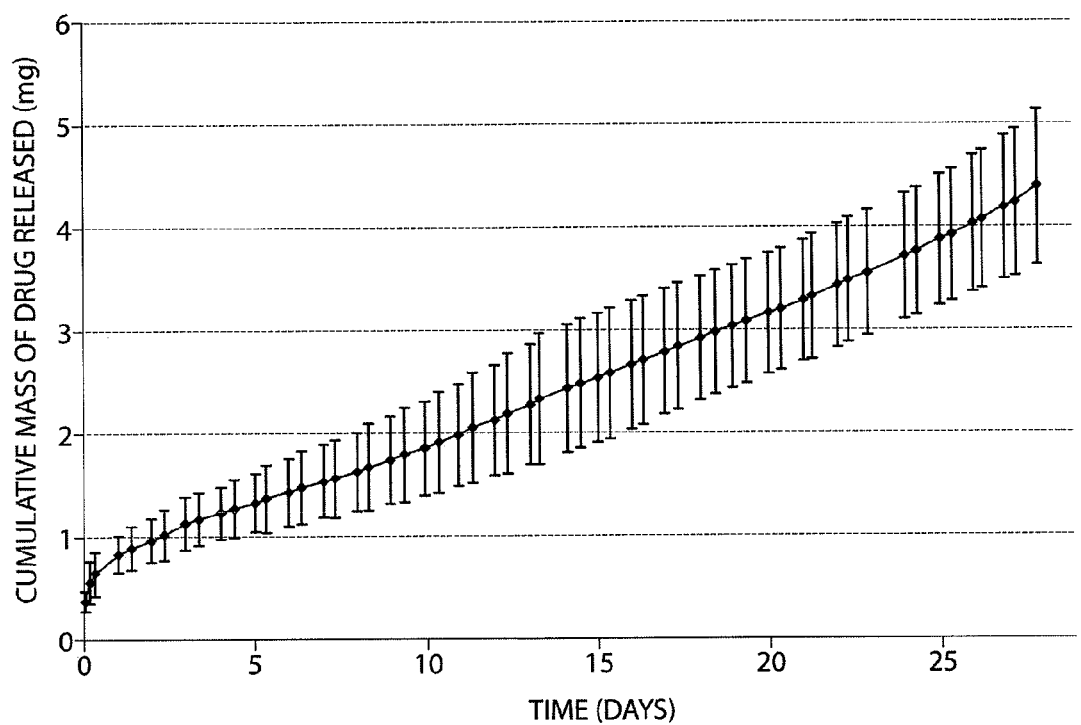
FIG. 6 is a graph illustrating ciprofloxacin release from pHEMA-encapsulated high molecular weight (118 kD) PLGA 65:35 films with a 1:1 PLGA:ciprofloxacin ratio. Data are means with standard deviations.

Anti-bacterial prototype contact lenses were fabricated by encapsulating ciprofloxacin-PLGA 65:35 (high [118 kDa] molecular weight) films in pHEMA. These prototypes also demonstrated a small initial burst of drug release in the first 24 hours, followed by over four weeks of substantially zero-order kinetics (FIG. 6). After the initial burst, each prototype contact lens released an average mass of 134 μg of ciprofloxacin per day. Over the course of a month, the lenses released 23% of the ciprofloxacin they initially contained.

Example 4

Antimicrobial Activity of Ciprofloxacin-PLGA Films

Ciprofloxacin-containing PBS samples were tested for antibacterial effectiveness against three clinical test isolates of ciprofloxacin-sensitive *S. aureus* and a ciprofloxacin-resistant *S. aureus*. The resistant strain served as a positive control to assure that the bacterial killing was due to the antibiotic and not to an unknown inhibitory material. All bacteria were grown in antibiotic-free brain heart infusion (BHI)-sucrose-PBS. Release media without bacteria were used as a negative control.

Bacteria were initially propagated from five large colonies and grown for two hours in 3 mL of antibiotic free 10% BHI-0.2% sucrose. The log phase (actively growing) bacterial suspensions were diluted 1:10 by adding 0.01 mL of the bacterial suspension to 0.09 mL of the ciprofloxacin release media. Samples were incubated at 37° C. for 20 hours, after which serial dilutions were plated on nonselective BHI agar without antibiotics at 37° C. for 48 hours to allow for slow-growing colonies to be recovered. Colonies that did grow were recultured and assessed for ciprofloxacin susceptibility on BHI agar with and without 50 μg/mL of ciprofloxacin. Each of the samples was tested in triplicate.

Ciprofloxacin that eluted from the prototype contact lenses had the same HPLC profile as that of Cipro™ I.V. The antibacterial effectiveness of ciprofloxacin released from the contact lenses was tested (Table 2) to confirm that it was not impaired by the numerous processing steps to which it was exposed (ultraviolet light, temperature and pH changes, and interaction with other materials) and by extended presence in solution at 37° C. The release medium was collected from four ciprofloxacin-containing lenses (same samples as FIG. 5) on the 28th day of release and tested against *Staphylococcus aureus* clinical isolates grown in antibiotic-free BHI-sucrose-PBS. In addition, samples were taken from one lens at days 2 and 14 of release. In all cases, the samples represented approximately 16 hours of release of drug.

With bacterial inocula of less than $10^5$ cells, there was complete inhibition of all three strains of ciprofloxacin-sensitive *S. aureus* (MEEI-IB003, MEEI-IB012, and MEEI-IB013) by the contact lens release media. Using bacterial inocula of $10^6$ cells or greater, there was still complete inhibition of ciprofloxacin-sensitive *S. aureus* at days 2, 15, and 28 of release (Table 2). The data in Table 2 reflects drug released over 16 hours preceding the stated time-point, and are averages of triplicates of single samples. At 28 days, the data are averaged from triplicates of four separate samples. At the higher bacterial inocula, there were rare bacterial isolates that grew, albeit with very low counts (30 or less, compared to billions in untreated controls) due to the development of resistance to ciprofloxacin.

TABLE 2

Growth of ciprofloxacin-resistant and -susceptible strains of *Staphlococcus aureus* after exposure to ciprofloxacin eluted from four separate prototype contact lenses.

| S. aureus Strain | Inoculum | Time point of ciprofloxacin release | | | No Ciprofloxacin |
| --- | --- | --- | --- | --- | --- |
| | | 2 days | 14 days | 28 days | |
| MEEI-IB01 (Ciprofloxacin Resistant) | $8.4 \times 10^6$ | $9.0 \times 10^9$ | $5.0 \times 10^9$ | $3.0 \times 10^9$-$1.0 \times 10^{10}$ | $4.0 \times 10^9$ |
| MEEI-IB003 (Ciprofloxacin Susceptible) | $6.6 \times 10^6$ | 0 | 0 | 0 | $2.0 \times 10^9$ |
| MEEI-IB012 (Ciprofloxacin Susceptible) | $8.5 \times 10^6$ | 0 | 0 | 0 | $1.5 \times 10^{10}$ |

TABLE 2-continued

Growth of ciprofloxacin-resistant and -susceptible strains of
*Staphlococcus aureus* after exposure to ciprofloxacin
eluted from four separate prototype contact lenses.

| Strain | *S. aureus* Inoculum | Time point of ciprofloxacin release | | | No Ciprofloxacin |
|---|---|---|---|---|---|
| | | 2 days | 14 days | 28 days | |
| MEEI-IB013 (Ciprofloxacin Susceptible) | $8.0 \times 10^6$ | 0 | 0 | 0 | $8.0 \times 10^9$ |
| No Bacteria | 0 | 0 | 0 | 0 | 0 |

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A drug-eluting contact lens comprising:
an optical pathway wherein a line of vision of a wearer of the contact lens passes through the optical pathway; and
a continuous drug carrying zone comprising at least one drug for release by the contact lens proximate an eye of the wearer, the zone surrounding the optical pathway but not residing in the optical pathway, wherein the drug carrying zone is encapsulated by a lens material.

2. A drug-eluting contact lens as in claim 1, wherein the drug carrying zone comprises a drug release material.

3. A drug-eluting contact lens as in claim 2, wherein the drug release material comprises a non-polymeric excipient.

4. A drug-eluting contact lens as in claim 2, wherein the drug release material comprises a multi-layered structure.

5. A drug-eluting contact lens as in claim 2, wherein the contact lens is dimensioned so that, when worn by a subject, the drug release material is positioned over the conjunctiva.

6. A drug-eluting contact lens as in claim 1, wherein the contact lens contains at least 1 mg of the at least one drug.

7. A drug-eluting contact lens as in claim 1, wherein the contact lens contains at least 100 mg of the at least one drug.

8. A drug-eluting contact lens as in claim 1, wherein the at least one drug comprises a first drug and a second drug, wherein the first drug is released at a different rate than the second drug.

9. A drug-eluting contact lens as in claim 1, wherein the at least one drug comprises an anti-infective agent, an anesthetic agent, an anti-VEGF agent, an anti-inflammatory agent, a biological agent, a keratitis treatment composition, and/or an intraocular pressure reducing agent.

10. A drug-eluting contact lens as in claim 1, wherein the at least one drug is released over a period of at least 720 hours.

11. A drug-eluting contact lens as in claim 1, wherein the at least one drug is released at a rate of at least 1 microgram per hour.

12. A drug-eluting contact lens as in claim 1, wherein the contact lens provides substantially zero-order release of the at least one drug over a period of at least 120 hours.

13. A drug-eluting contact lens as in claim 1, wherein the at least one drug is released at a rate of at least 0.005 micrograms per hour.

14. A drug-eluting contact lens as in claim 1, wherein the contact lens provides substantially zero-order release of the at least one drug over a period of at least 168 hours.

15. A drug-eluting contact lens as in claim 1, wherein the contact lens provides substantially zero-order release of the at least one drug over a period of at least 720 hours.

16. A drug-eluting contact lens as in claim 1, wherein the contact lens provides substantially zero-order release of the at least one drug over a period of at least 2160 hours.

17. A drug-eluting contact lens as in claim 1, wherein the contact lens provides substantially zero-order release of the at least one drug over a period of at least 2880 hours.

18. A drug-eluting contact lens as in claim 1, wherein the contact lens provides substantially zero-order release of the at least one drug over a period of at least 4800 hours.

19. A drug-eluting contact lens as in claim 1, wherein the contact lens provides substantially zero-order release of the at least one drug over a period of at least 9600 hours.

20. A drug-eluting contact lens as in claim 2, wherein the drug release material comprises a polymer.

21. A drug-eluting contact lens comprising:
a hydrogel lens material encapsulating a drug-containing polymer film containing at least one drug,
wherein the contact lens provides substantially zero-order release of the at least one drug for at least 168 hours.

22. A drug-eluting contact lens as in claim 21, wherein the contact lens is structured and dimensioned so that, when worn by a subject, the hydrogel lens material crossing an optical axis of the subject is optically transparent.

23. A drug-eluting contact lens as in claim 21, wherein the contact lens contains at least 1 mg of the at least one drug.

24. A drug-eluting contact lens as in claim 21, wherein the contact lens contains at least 10 mg of the at least one drug.

25. A drug-eluting contact lens as in claim 21, wherein the contact lens provides substantially zero-order release of the at least one drug over a period of at least 720 hours.

26. A drug-eluting contact lens as in claim 21, wherein the at least one drug is released at a rate of at least 0.1 micrograms per hour.

27. A drug-eluting contact lens comprising:
a hydrogel lens material encapsulating a drug-containing polymer film containing at least one drug,
wherein the contact lens provides release of the at least one drug at therapeutically effective amounts for at least 168 hours.

28. A drug-eluting contact lens as in claim 27, wherein the contact lens is structured and dimensioned so that, when worn by a subject, the hydrogel lens material crossing an optical axis of the subject is optically transparent.

29. A drug-eluting contact lens as in claim 27, wherein the contact lens contains at least 1 mg of the at least one drug.

30. A drug-eluting contact lens as in claim 27, wherein the contact lens contains at least 10 mg of the at least one drug.

31. A drug-eluting contact lens as in claim 27, wherein the contact lens provides release of the at least one drug at therapeutically effective amounts for at least 720 hours.

32. A drug-eluting contact lens as in claim 27, wherein the at least one drug is released at a rate of at least 0.1 micrograms per hour.

* * * * *